United States Patent
Klok et al.

(10) Patent No.: US 9,902,975 B2
(45) Date of Patent: Feb. 27, 2018

(54) PROCESS FOR THE BIOLOGICAL CONVERSION OF BISULPHIDE INTO ELEMENTAL SULPHUR

(71) Applicant: PAQELL B.V., Amsterdam (NL)

(72) Inventors: Johannes Bernardus Maria Klok, Amsterdam (NL); Albert Joseph Hendrik Janssen, Geldermalsen (NL); Gijsbert Jan Van Heeringen, Amsterdam (NL); Jan-Henk Van Dijk, Amsterdam (NL)

(73) Assignee: PAQELL B.V., Amsterdam (NL)

( * ) Notice: Subject to any disclaimer, the term of this patent is extended or adjusted under 35 U.S.C. 154(b) by 11 days.

(21) Appl. No.: 15/115,767

(22) PCT Filed: Jan. 30, 2015

(86) PCT No.: PCT/EP2015/051872
§ 371 (c)(1),
(2) Date: Aug. 1, 2016

(87) PCT Pub. No.: WO2015/114069
PCT Pub. Date: Aug. 6, 2015

(65) Prior Publication Data
US 2017/0009258 A1    Jan. 12, 2017

(30) Foreign Application Priority Data

Feb. 3, 2014  (EP) .................................... 14153663
Jul. 18, 2014  (EP) .................................... 14177741

(51) Int. Cl.
| | | |
|---|---|---|
| C12P 3/00 | (2006.01) | |
| C02F 3/34 | (2006.01) | |
| B01D 53/84 | (2006.01) | |
| C01B 17/05 | (2006.01) | |
| B01D 53/48 | (2006.01) | |
| C02F 101/10 | (2006.01) | |
| C02F 103/18 | (2006.01) | |

(52) U.S. Cl.
CPC ................ *C12P 3/00* (2013.01); *B01D 53/48* (2013.01); *B01D 53/84* (2013.01); *C01B 17/05* (2013.01); *C02F 3/345* (2013.01); *B01D 2251/95* (2013.01); *C02F 2101/101* (2013.01); *C02F 2103/18* (2013.01)

(58) Field of Classification Search
None
See application file for complete search history.

(56) References Cited

U.S. PATENT DOCUMENTS

2008/0190844 A1    8/2008    Haase

FOREIGN PATENT DOCUMENTS

| EP | 0451922 | 10/1991 |
|---|---|---|
| WO | 9630110 | 10/1996 |
| WO | 2004056454 | 7/2004 |

*Primary Examiner* — Christian Fronda
(74) *Attorney, Agent, or Firm* — Nixon Peabody LLP (57) ABSTRACT

The invention is directed to a process for the biological conversion of bisulphide into elemental sulphur, comprising the following steps: a) converting bisulphide as dissolved in an aqueous solution to elemental sulphur in the presence of sulphide-oxidizing bacteria and under anaerobic conditions to obtain a first liquid effluent comprising elemental sulphur and used sulphide-oxidizing bacteria; b) regenerating the used sulphide-oxidizing bacteria as obtained in step (a) and as comprised in an aqueous solution in the presence of an oxidant to obtain a second liquid effluent comprising regenerated sulphide-oxidizing bacteria; c) separating elemental sulphur from either the first and/or the second liquid effluent; d) using the regenerated sulphide-oxidizing bacteria in step (a) as the sulphide-oxidizing bacteria.

22 Claims, 2 Drawing Sheets

PROCESS FOR THE BIOLOGICAL CONVERSION OF BISULPHIDE INTO ELEMENTAL SULPHUR

CROSS REFERENCE TO RELATED APPLICATIONS

This application is a 371 National Phase Entry of International Patent Application No. PCT/EP2015/051872 filed Jan. 30, 2015 claims benefit of EP 14153663.1 filed Feb. 3, 2014 and EP 14177741.7 filed Jul. 18, 2014, the contents of which are incorporated herein by reference in their entirety.

FIELD OF THE INVENTION

The present invention relates to a process for the biological conversion of bisulphide into elemental sulphur. In particular, the invention relates to a process for the treatment of a gas stream comprising sulphur compounds including hydrogen sulphide, also referred to as a sour gas stream, wherein the gas stream is contacted in an absorption column with a liquid alkaline absorbent to obtain a treated gas stream and a liquid alkaline absorbent comprising bisulphide and wherein the bisulphide in the liquid alkaline absorbent is biologically converted into elemental sulphur using sulphide-oxidising bacteria.

BACKGROUND OF THE INVENTION

Processes for the biological conversion of bisulphide into elemental sulphur by means of sulphide-oxidising bacteria are well-known in the art. Typically in such processes, a liquid alkaline absorbent that has been used for absorption of hydrogen sulphide from a sour gas stream and that comprises absorbed hydrogen sulphide, predominantly in the form of bisulphide but typically also to some extent sulphide, polysulphide and/or dissolved hydrogen sulphide, is contacted with sulphide-oxidising bacteria for conversion of dissolved sulphides (mainly as bisulphide) into elemental sulphur. Bisulphide in other streams, for example in a spent caustic stream, may also be converted into elemental sulphur in such biological conversion processes.

Processes comprising a sour gas absorption stage followed by biological oxidation of the dissolved sulphides are for example disclosed in WO92/10270, WO94/29227, WO98/57731, US2008/0190844 and WO2005/092788.

In the prior art processes, the bisulphide-containing alkaline absorbent obtained by sour gas absorption is contacted with sulphide-oxidising bacteria in an aerobic bioreactor in order to convert the bisulphide into elemental sulphur and to obtain regenerated absorbent that is recycled to the absorption stage. Elemental sulphur is recovered from part of the regenerated absorbent.

In the process of US2008/190844 a process is described in which the biomass and the aqueous solution as present in the effluent of a so-called aerobic Sulphur Biological Reactor are separated with the aid of a cationic coagulating agent. The biomass may be recycled to the reactor and the aqueous solution may be recycled to the sour gas absorber or scrubber. This aqueous solution, which does not comprise any biomass, may be processed in an Aerobic Biological Reactor.

In the process as for example disclosed in WO94/29227, dissolved sulphides are oxidised with sulphide-oxidising bacteria. It is mentioned in WO94/29227 that the sulphide volume load to the bioreactor is preferably below 1000 mg/l·h, more preferably below 200 mg/l·h, to avoid an excessively high effluent sulphide concentration. In biological sulphide oxidation processes, the biological oxidation to higher oxidised sulphur compounds such as sulphate or the chemical oxidation to thiosulphate is preferably prevented. It is mentioned in WO94/29227 that the oxidation to higher oxidised sulphur compounds can be substantially reduced by adjusting the oxygen supply to the bioreactor. A preferred range of 0.5 to 1.5 moles of oxygen per mole of sulphide is mentioned.

In practice it has, however, been found that even in situations where the amount of oxygen supplied to the bioreactor has been controlled within the range of 0.5 to 1.5 moles of oxygen per mole of sulphide, undesirably high amounts of sulphate and thiosulphate can be formed. There is thus a need in the art for improved prevention of (thio)sulphate formation.

SUMMARY OF THE INVENTION

This aim is achieved by the following process. A process for the biological conversion of bisulphide into elemental sulphur, comprising the following steps:

a) converting bisulphide as dissolved in an aqueous solution to elemental sulphur in the presence of sulphide-oxidising bacteria and under anaerobic conditions to obtain a first liquid effluent comprising elemental sulphur and used sulphide-oxidising bacteria;

b) regenerating the used sulphide-oxidising bacteria as obtained in step (a) and as comprised in an aqueous solution in the presence of an oxidant to obtain a second liquid effluent comprising regenerated sulphide-oxidising bacteria;

c) separating elemental sulphur from either the first and/or the second liquid effluent;

d) using the regenerated sulphide-oxidising bacteria in step (a) as the sulphide-oxidising bacteria.

Applicants found that the selectivity towards elemental sulphur is significantly increased and the formation of the undesired sulphate and thiosulphate is reduced when the biological oxidation of bisulphide to elemental sulphur is carried out according to the above process. A further advantage of the process is that the content of bisulphide in the aqueous solution in step (a) may be higher than in previous processes without generating high amounts of thiosulphate as the by-product. This is advantageous because it for example reduces the size of reactor equipment or increases the capacity in existing equipment. Applicants found that bisulphide can be selectively oxidised to elemental sulphur by sulphide-oxidising bacteria under anaerobic conditions, i.e. in the absence of molecular oxygen.

An important advantage of the process according to the invention is that the biologic formation of sulphate is significantly reduced and the selectivity towards elemental sulphur significantly increased. Without wishing to be bound to any theory, it is believed that the exposure of the sulphide-oxidising bacteria to bisulphide in the presence of elemental sulphur under anaerobic conditions in the first stage, results in the suppression of enzyme systems in the sulphide-oxidising bacteria that are involved in the conversion of bisulphide into sulphate in favour of enzyme systems involved in the selective oxidation of bisulphide and/or polysulphides into elemental sulphur.

Also the formation of thiosulphate due to chemical oxidation of bisulphide is significantly reduced compared to prior art biological sulphide-oxidising processes as no direct contact occurs between a solution high in bisulphides and molecular oxygen.

A further advantage of the process according to the invention is that due to the lower formation of undesired oxidation products such as sulphate and thiosulphate, the bleed stream that needs to be purged from the process to avoid a too large built-up of undesired compounds can be reduced and therewith a larger amount of sulphide-oxidising bacteria is maintained in the process and less make-up chemicals, like the optional alkalines, need to be added to the process.

It has further been found that the elemental sulphur formed in the process according to the invention shows improved precipitation compared to the elemental sulphur formed in prior art single step biological oxidation processes. Further advantages will be described below.

DETAILED DESCRIPTION OF THE INVENTION

Without wishing to be bound to any theory, it is believed that in step (a), which will also be referred to as the first bioreaction zone, bisulphide reacts with elemental sulphur to form polysulphide, and that bisulphide and/or polysulphide are at least partly biologically oxidised into elemental sulphur whilst electron acceptors in the sulphide-oxidising bacteria take up the electrons that result from the oxidation reaction until such acceptors are completely reduced, resulting in so-called reduced state bacteria. In step (b), which will also be referred to as the second bioreaction zone, the bacteria are regenerated, i.e. they are brought from a reduced state into an oxidised state. It is believed that in this stage the electron acceptors donate electrons to the oxidant and are therewith regenerated so that they can thereafter oxidise bisulphide and/or polysulphide in the absence of molecular oxygen again.

Applicants believe that by treating the bacteria, in a process according to the invention, conditions are created which favor the existence of a sub-population of bacteria which have a low selectivity to sulphate and a high selectivity to elemental sulphur starting from bisulphide.

The invention is thus also directed to a method to optimise an existing aerobic process comprising x1 an aerobic bio-reactor comprising sulphide-oxidising bacteria, x2 a sulphur separation step, x3 a sulphide-oxidising bacteria recycle from x2 to x1, wherein an anaerobic reactor is added as part of x3 and performing the process according to the present invention.

If the existing aerobic process comprises an absorption column having a feed inlet for sour gas at its lower end and a liquid feed inlet for a liquid comprising sulphide-oxidising bacteria at its upper end then the optimising method may suitably be performed as follows: by repositioning the gas inlet of the sour gas in the column to a more elevated height and adding a second inlet for a liquid feed comprising sulphide-oxidising bacteria to a less elevated height with respect to the existing inlet. This creates an anaerobic reactor X3 in the lower part of the column.

Accordingly, the invention relates to a process for the biological conversion of bisulphide into elemental sulphur, comprising the following steps:

i) providing an aqueous solution comprising bisulphide;

ii) supplying the aqueous solution comprising bisulphide to a first bioreaction zone, wherein the bisulphide is converted into elemental sulphur in the absence of molecular oxygen and in the presence of sulphide-oxidising bacteria, to obtain a liquid first bioreaction zone effluent comprising elemental sulphur and sulphide-oxidising bacteria;

iii) supplying the liquid first bioreaction zone effluent to a second bioreaction zone for regeneration of the sulphide-oxidising bacteria, wherein an oxidant is supplied to the second bioreaction zone, to obtain a liquid second bioreaction zone effluent comprising elemental sulphur and regenerated sulphide-oxidising bacteria;

iv) recycling at least part of the liquid second bioreaction zone effluent comprising elemental sulphur and regenerated sulphide-oxidising bacteria to the first bioreaction zone.

The process according to the invention is a process for the biological conversion of bisulphide into elemental sulphur. The process comprises providing an aqueous solution comprising bisulphide and supplying the aqueous solution to a first bioreaction zone to perform step (a), wherein the bisulphide is converted into elemental sulphur in the absence of molecular oxygen and in the presence of sulphide-oxidising bacteria. In the first bioreaction zone, a first liquid effluent is obtained that comprises elemental sulphur and sulphide-oxidising bacteria. The first liquid effluent is supplied to a second bioreaction zone for regeneration of the sulphide-oxidising bacteria as in step (b). An oxidant, such as for example nitrate or molecular oxygen, preferably molecular oxygen, is supplied to the second bioreaction zone and a second liquid effluent is obtained that comprises regenerated sulphide-oxidising bacteria and elemental sulphur. In a step (c) elemental sulphur is separated from either the first and/or the second liquid effluent. In step (d), the liquid second bioreaction zone effluent is recycled, directly and/or indirectly, to the first bioreaction zone.

The process may be performed as a continuous process, a batch process or as a semi-batch process. Preferably the process as here described is performed as a continuous process. If the sulphide-oxidising bacteria are immobilized on a carrier in a reactor a blocked-out mode of operation will be necessary to alternatingly perform step (a) and (b) in the same reactor.

Reference herein to bisulphide is to the inorganic anion with the chemical formula $HS^-$, which may derive from any form of sulphide, including sulphide anions, bisulphide, hydrogen sulphide, polysulphide, and organic sulphides such as lower alkyl mercaptans and carbon disulphide.

The aqueous solution comprising bisulphide used in step (a) may be any aqueous solution comprising bisulphide from which bisulphide needs to be removed, such as for example a spent caustic solution or an alkaline absorbing solution used for absorbing hydrogen sulphide or other reduced sulphur compounds from a sour gas stream. Alternatively, the aqueous solution comprising bisulphide may be a bisulphide solution obtained by dissolving hydrogen sulphide from a highly concentrated or essentially pure hydrogen sulphide gas into an aqueous solution by means of an ejector.

Preferably, the aqueous solution comprising bisulphide provided in step a) is a liquid alkaline absorbent comprising bisulphide obtained in the treatment of a sour gas stream. In that case, step a) comprises supplying a gas stream comprising sulphur compounds including hydrogen sulphide to an absorption column via an inlet for gas, and contacting the gas stream in the absorption column with a liquid alkaline absorbent to obtain a treated gas stream and a liquid alkaline absorbent comprising bisulphide. The liquid alkaline absorbent comprising bisulphide may be contacted with the sulphide-oxidising bacteria to perform step (a).

Preferably the liquid alkaline absorbent may also comprise of part of the regenerated sulphide-oxidising bacteria. If these bacteria are present the above absorption part of step (a) may be performed simultaneously. The absorption is suitably performed under anaerobic conditions. The sour gas thus preferably does not contain oxygen in any significant amount. Preferably such an absorption is performed in an absorption column wherein the sour gas stream is contacted in the absorption column with all or preferably part of the second liquid effluent as obtained in step (b) which second liquid is provided to an upper part of the absorption column. The second liquid effluent is thereby indirectly recycled to the first bioreaction zone, i.e. via the absorption column by recycling at least part of the liquid second bioreaction zone effluent to an upper part of the absorption column. The second liquid may, before being recycled to the absorption column and/or to step (a), be subjected to one or more of the process steps described below, for example step (c) or the optional purge.

Applicants found that the removal of dissolved bisulphide from the aqueous solution by biological remediation by the sulphide-oxidising bacteria is performed rapidly under the anaerobic conditions of step (a) and may even occurs during the liquid alkaline absorption process. This feature of the process results in an even more efficient liquid alkaline absorption. This active absorption results in that only a relatively short contact time is required between sour gas and the alkaline absorbent comprising the regenerated sulphide-oxidising bacteria to absorb a sufficient amount of hydrogen sulphide from the sour gas stream. Advantageously, size and volume of the absorption column and the amount of alkaline absorbent needed can be reduced. This is especially advantageous when the sour gas stream also comprises carbon dioxide. By being able to reduce the contact time in the absorption column less carbon dioxide absorption takes place and an undesired decrease of pH of the liquid alkaline absorbent is avoided.

In such process, at least part of the second liquid effluent is indirectly recycled to step (a), i.e. the first bioreaction zone, by first recycling at least part of the second liquid effluent to an upper part of the absorption column. Since the liquid alkaline absorbent comprising bisulphide obtained in the absorption column is subsequently used in step (a) step (d) is performed.

The bisulphide concentration in the aqueous solution supplied to step (a) is not critical in the process according to the invention. Solutions with bisulphide concentrations (expressed as sulphur) as high as 20 grams per liter or even higher may be used. Preferably, the bisulphide concentration in the aqueous solution is in the range of from 100 mg/L to 15 g/L, more preferably of from 150 mg/L to 10 g/L. The afore mentioned bisulphide concentration includes dissolved bisulphide and bisulphide which is absorbed by and/or converted to elemental sulphur by the sulphide-oxidising bacteria.

In a preferred embodiment of the process according to the invention comprises an additional step which comprises contacting a gas stream comprising sulphur compounds including hydrogen sulphide in an absorption column with a liquid alkaline absorbent to obtain a treated gas stream and a liquid alkaline absorbent comprising bisulphide as described above. Such alkaline absorption step for absorption of sulphide is well known in the art. Process conditions for such step are well-known in the art and generally include a temperature in the range of from 0° C. to 100° C., preferably of from 20° C. to 80° C., more preferably of from 25° C. to 60° C. and a pressure in the range of from 0 bara to 100 bara, preferably of from atmospheric pressure to 80 bara.

The liquid alkaline absorbent may be any liquid alkaline absorbent known to be suitable for absorption of hydrogen sulphide, i.e. known to dissolve sulphides. Examples of suitable liquid alkaline absorbents are carbonate, bicarbonate and/or phosphate solutions, more preferably a buffered solution comprising carbonate and bicarbonate. Buffered solutions comprising sodium and/or potassium carbonate and bicarbonate are particularly preferred, more in particular a buffered solution comprising sodium carbonate and sodium bicarbonate. The pH of the liquid alkaline absorbent that is supplied to the upper part of the absorption column, is preferably in the range of from 7 to 10, more preferably of from 7.5 to 9.5. It will be appreciated that in downward direction of the column, the pH of the absorption liquid will decrease due to absorption of acidic compounds from the gas stream, in particular hydrogen sulphide and carbon dioxide. The pH of the liquid alkaline solution comprising bisulphide that is obtained and discharged from the column and supplied to or used in step (a) is therefore lower than the inlet pH of the liquid alkaline absorbent in the absorption column. The pH of the liquid alkaline solution comprising bisulphide supplied to or used in step (a), the first bioreaction zone, may be as low as 6.5 and is preferably in the range of from 6.5 to 9.0.

Step (a) of the process according to the invention may involve supplying an aqueous solution comprising bisulphide provided, for example the loaded liquid alkaline absorbent as obtained in an absorption step, to a first bioreaction zone comprising sulphide-oxidising bacteria. Optionally all or part of the regenerated sulphide-oxidising bacteria may already be present in the loaded liquid alkaline absorbent as described above. In the first bioreaction zone, sulphide-oxidising bacteria may be dispersed in an aqueous reaction medium, typically the aqueous solution to be treated. Step (a) is performed under anaerobic conditions. With anaerobic conditions is meant in the absence of molecular oxygen and no molecular oxygen is supplied to the first bioreaction zone. In the first bioreaction zone, bisulphide is converted into elemental sulphur in the absence of molecular oxygen, preferably also in the absence of other oxidants such as for example nitrate. Reference herein to 'in the absence of molecular oxygen' is to a concentration of molecular oxygen in the aqueous reaction medium of at most 10 µM molecular oxygen, preferably at most 1 µM, more preferably at most 0.1 µM molecular oxygen.

The sulphide-oxidising bacteria may be any sulphide-oxidising bacteria, preferably sulphide-oxidising bacteria of the genera *Halothiobacillus, Thioalkalimicrobium, Thioal-*

*kalispira, Thioalkalibacter, Thioalkalivibrio* and related bacteria. The bacteria may be used as such, or may be supported on a dispersed carrier.

The conversion in step (a), the first bioreaction zone, may take place at any suitable conditions of temperature, pressure and hydraulic residence time for biological oxidation of bisulphide into elemental sulphur. Preferably, the first bioreaction zone is operated at a temperature in the range of from 10 to 60° C., more preferably of from 20 to 40° C. The first bioreaction zone is preferably operated at a pressure in the range of from 0 bara to 100 bara, more preferably of from atmospheric pressure to 80 bara.

Preferably, the aqueous reaction medium in step (a), the first bioreaction zone, has a pH in the range of from 7 to 10, more preferably in the range of from 7.5 to 9.5. The aqueous reaction medium may comprise trace compounds, such as for example iron, copper or zinc, as nutrients for the sulphide-oxidising bacteria.

The residence time of the sulphide-oxidising bacteria in step (a), the first bioreaction zone, is preferably at least 3 minutes, more preferably at least 5 minutes, more preferably at least 10 minutes. The maximum residence time is not critical, but for practical reasons, the residence time is preferably at most 2 hours, more preferably at most 1 hour.

In step (a) suitably more than 80 mol %, preferably more than 90 mol % and even more preferably more than 95 mol % of the dissolved bisulphide is removed from the aqueous solution by biological remediation by the sulphide-oxidising bacteria in step (a). In case of a separate absorption step part of the dissolved bisulphide will already be removed during this absorption step when the alkaline absorbent comprises regenerated sulphide-oxidising bacteria. The percentages of removal will then be based on the total bisulphide as absorbed in the absorption step. The actual conversion to elemental sulphur which takes place within the bacteria may take place in step (a), in step (b) or in the transport between steps (a) and (b).

In step (a), the first bioreaction zone, elemental sulphur is formed by selective oxidation of bisulphide, probably via polysulphide as intermediate product, to elemental sulphur. Thus, a first liquid effluent comprising elemental sulphur and sulphide-oxidising bacteria is obtained. The effluent may be directly supplied to step (b), the second bioreaction zone, for regeneration of the sulphide-oxidising bacteria, i.e. to bring the bacteria in an oxidised state. By directly supplied is here meant that no intermediate process step is performed with the object to remove elemental sulphur and/or sulphide-oxidising bacteria from the first liquid effluent. Optionally elemental sulphur may be removed from the first liquid effluent. In such a step some of the sulphide-oxidising bacteria may also be removed from the first liquid effluent. However it is preferred to avoid the loss of sulphide-oxidising bacteria in such a step and ensure that the majority of these bacteria are provided to step (b), the second bioreaction zone. Preferably, the liquid first bioreaction zone effluent that is supplied to the second bioreaction zone comprises less than 5 mM dissolved bisulphide, more preferably is essentially free of dissolved bisulphide. The low content of dissolved bisulphide is advantageous to avoid the sulphate formation under the aerobic conditions of step (b). It is further believed that the low bisulphide content avoids the growth of the bacteria population which seem to be responsible for the formation of sulphate in either step (a) or (b) and avoids the chemical oxidation to thiosulphate.

In order to regenerate the bacteria, an oxidant is present in step (b) as for example supplied to the second bioreaction zone. Any suitable oxidant may be used, for example nitrate or molecular oxygen, preferably molecular oxygen. The oxidant may be supplied to the second bioreaction zone in any suitable way, preferably by supplying a gaseous stream comprising molecular oxygen to the second bioreaction zone. The gaseous stream comprising molecular oxygen may be any suitable gas comprising oxygen, preferably air. Preferably, the amount of oxidant supplied to the second bioreaction zone is at least about the stoichiometric amount needed for oxidation of the sulphide supplied to the first bioreaction zone into elemental sulphur. It has been found that the effluent of the first bioreaction zone comprises no or a very low amount of bisulphide. Therefore, no or a very low amount of bisulphide is supplied to the second bioreaction zone via the first liquid effluent. Due to this low amount of bisulphide, the amount of oxidant supplied to the second bioreaction zone is not critical. Even if an amount above the stoichiometric amount per mole bisulphide to be converted is supplied to the second reaction zone, formation of large amounts of undesired sulphur compounds such as sulphate and thiosulphate may be avoided.

If a gaseous stream comprising molecular oxygen is supplied to the second bioreaction zone, such stream advantageously strips carbon dioxide from the second reaction zone and as a result the pH of the reaction medium in the second bioreaction zone is increased.

The regeneration of the sulphide-oxidising bacteria in step (b) may take place at any conditions of temperature, pressure and hydraulic residence time known to be suitable for biological oxidation of bisulphide into elemental sulphur of the prior art aerobic or quasi-aerobic processes. Preferably, the second bioreaction zone is operated at a temperature in the range of from 10 to 60° C., more preferably of from 20 to 40° C. The second bioreaction zone is preferably operated at a pressure in the range 0 bara to 10 bara, more preferably of from atmospheric pressure to 5 bara, even more preferably at atmospheric pressure.

In step (b), a second liquid effluent is obtained that comprises elemental sulphur and regenerated sulphide-oxidising bacteria. The second liquid bioreaction zone effluent is at least partly recycled to step (a), the first bioreaction zone, in order to perform step (d), wherein the first bioreaction zone is provided with regenerated bacteria. In the preferred embodiment wherein the process comprises an absorption step for absorption of sulphide from a sour gas stream, at least part of the second liquid effluent is indirectly recycled to step (a), the first reaction zone, by first recycling at least part of the second liquid effluent to an upper part of the absorption column as used in the absorption step. In this preferred embodiment with an absorption column, preferably another part of the second liquid effluent is directly recycled to step (a), the first bioreaction zone. By such direct recycle, the concentration of regenerated bacteria in step (a), the first bioreaction zone, can be maintained at a higher level. Moreover, such direct recycle will result in an increased pH in step (a), the first bioreaction zone, since the pH in the second bioreaction zone is typically higher than the pH in the lower part of the absorption column, in particular in case a sour gas stream with a relatively high carbon dioxide content is treated in the absorption column. Thus the loaded liquid as obtained in the lower part of the absorption column which may have a lower pH will then be mixed with directly recycled second liquid effluent having a higher pH to obtain the aqueous liquid in which step (a) is performed.

As described above it may be advantageous that an absorption step of a sour gas and step (a) is performed in a single absorption column. In such an embodiment the second liquid effluent is provided to the column at different heights along the column. The sour gas may be supplied to the lower part of the column and/or to an intermediate position or positions. The volume of second liquid effluent provided to the top part of the column should be sufficiently high to absorb the required amount of sulphur compounds from the sour gas as bisulphide. The volume of second liquid effluent comprising regenerated sulphide-oxidising bacteria provided to the lower part of the column should be sufficiently high to achieve that bisulphide is sufficiently converted to elemental sulphur in the first liquid effluent as will be discharged at the lower end of the column. For this reason no or very little sour gas will be provided to this lower part of the column. Mixing may be enhanced by means of static mixers or mechanically operated mixers present in said lower part of the column.

The first and the second bioreaction zones may be two separate reaction zones in a single reactor, may each be contained in a separate reactor, or, as described above, the first bioreaction zone may be contained as part of an absorption column and especially in the lower part of the absorption column and the second bioreaction zone in a separate reactor. Preferably, the first and the second bioreaction zones are each contained in a separate bioreactor or in a separate absorption column and bioreactor. The first and the second bioreaction zones or bioreactors may each have any suitable configuration. Preferably each of the reaction zones or bioreactors has a configuration wherein back-mixing occurs. More preferably, each of the reaction zones has the configuration of a Continuously Stirred Tank Reactor (CSTR). If the absorption column is operated at an elevated pressure it may be desirable to operate the bioreactors at a more atmospheric pressure. Suitably the first bioreaction zone, step (a), may then be performed in a flash vessel. The flash vessel is suitably large enough to ensure enough residence time to perform step (a). In order to avoid losses of bisulphide in the flashed gas a recontactor is suitably used. In this recontactor the flashed gas may be contacted with the second liquid effluent.

Optionally, the liquid second bioreaction zone effluent is subjected to degassing before recycling such stream to the upper part of the absorber or to the first bioreaction zone.

The process according to the invention is preferably a continuous process. Once the process has been started-up and is running under steady state conditions, there is preferably a continuous supply of aqueous solution comprising bisulphide to the first bioreaction zone, of liquid first bioreaction zone effluent to the second bioreaction zone and of liquid second bioreaction zone effluent to the first bioreaction zone, more preferably partly via an absorption column.

Preferably, the process comprises a step c) wherein elemental sulphur is recovered from the process. Elemental sulphur may be recovered from different process streams, such as for example from the liquid second bioreaction zone effluent or from the liquid first bioreaction effluent. Preferably, elemental sulphur is recovered from at least part of the second liquid effluent while another part is recycled to the absorption column and/or the first bioreaction zone, i.e. step (a). Separation of elemental sulphur from an aqueous stream is well-known in the art. This may be done by any means known in the art, such as for example by means of sedimentation or other means for solid-liquid separation known in the art. If elemental sulphur is recovered from the second liquid effluent, elemental sulphur and a sulphur-depleted second effluent are obtained. Preferably, at least part of the sulphur-depleted second effluent thus obtained is recycled to the process, for example to the absorption column, to the first bioreaction zone and/or to the second bioreaction zone, more preferably to the second bioreaction zone as shown in Figures.

Although the formation of undesired higher oxidised sulphur compounds such as sulphate and thiosulphate are importantly reduced compared to prior art biological sulphide oxidation processes, some higher oxidised sulphur compounds may still be formed, in particular in step (b), the second bioreaction zone. In order to avoid undesired built-up of higher oxidised sulphur compounds in the process, part of the second liquid effluent, or of the sulphur-depleted second effluent obtained after elemental sulphur recovery from the second bioreaction effluent, is preferably purged from the process as a bleed stream. In order to minimise loss of sulphide-oxidising bacteria with the bleed stream, the part of the effluent that is purged from the process is preferably first subjected to a membrane separation step to obtain a retentate stream comprising sulphide-oxidising bacteria and a permeate stream that is essentially free of sulphide-oxidising bacteria. The retentate stream is recycled to the process and the permeate stream is purged from the process. In case such membrane separation step is applied, preferably sulphur-depleted second effluent is purged from the process in order to prevent fouling of the membrane by elemental sulphur. In the membrane separation step, any suitable membrane may be used. Preferably, ultra-filtration membranes are used. Because the formation of higher oxidised sulphur compounds is very much reduced the purge is relatively small. Applicants found that the loss of sulphide-oxidising bacteria via this purge may be compensated by the growth of the bacteria population in the process. This is advantageous because the above described membrane separation step and its complex processing can be avoided.

In the preferred embodiment of the process comprising an absorption step and wherein at least part of the second liquid effluent is recycled to the absorption column, it is believed that the regenerated sulphide-oxidising bacteria present in the absorption column, actively absorb bisulphide and/or polysulphide from the absorbent liquid. Because the second liquid effluent will comprise zero to very low contents of dissolved bisulphide a favorable absorption of bisulphide from the sour gas stream is possible. It case the second liquid effluent to be recycled comprises some bisulphide, it may be advantageous to subject the recycle stream to an oxidation/stripping step prior to recycling, in order to further oxidise bacteria and/or bisulphide and therewith increase the bisulphide absorption capacity of the recycled absorbent.

The sour gas stream that is contacted with the liquid alkaline absorbent may be any gaseous stream comprising sulphur compounds including hydrogen sulphide, optionally in combination with carbon dioxide. The gas stream may comprise sulphur compounds other than hydrogen sulphide, for example lower alkyl mercaptans or carbonyl sulphide. The gas stream may comprise hydrogen sulphide in any suitable amount ranging up to 100 vol % and for example be a sour gas stream with a high concentration of hydrogen sulphide, for example 30 vol. % or more and especially between 30 and 100 vol %. It is believed that the process conditions of the process according to the invention, in particular the exposure to bisulphide under anaerobic conditions in the first bioreaction zone, result in the selection of sulphide-oxidising bacteria that actively absorb bisulphide in the absence of molecular oxygen. Therefore, bisulphide is actively absorbed in the absorption column. The residence time in the absorption column needed for sufficient removal of hydrogen sulphide from the gas stream is therefore relatively short, thus avoiding too much carbon dioxide absorption and therewith a too large pH decrease of the liquid absorbent. This allows treatment of gas streams further comprising carbon dioxide, even in relative high concentrations, such as for example up to 20 vol % and even more especially between 5 and 20 vol. % in case the gas stream is natural gas. Examples of suitable sour gas streams comprising hydrogen sulphide include sour natural gas, synthesis gas, acid gas, geothermal gas, landfill gas, refinery gas, biogas and acid gas obtained in an amine gas treating process. The hydrogen sulphide as may be present in such gasses may be separated from these gasses and converted to elemental sulphur with the above process.

Gas streams comprising substantially of only hydrogen sulphide may be directly fed to the first bioreaction zone of step (a). Suitably the bisulphide comprising aqueous solution of step (a) is obtained by directly supplying a hydrogen sulphide comprising gas to a vessel in which step (a) is performed. Such a gas stream should not contain any significant amounts of molecular oxygen. This to maintain the anaerobic conditions of step (a). Suitably such gas streams may comprise for more than 80 vol %, preferably more than 90 vol % and even more preferably for more than 99 vol % of $H_2S$. This may be performed by adding the H2S gas to a continuously stirred tank reactor in which step (a) is performed. In such a process no absorption in an absorption column as described above is performed.

DETAILED DESCRIPTION OF THE DRAWINGS

Figure 1:
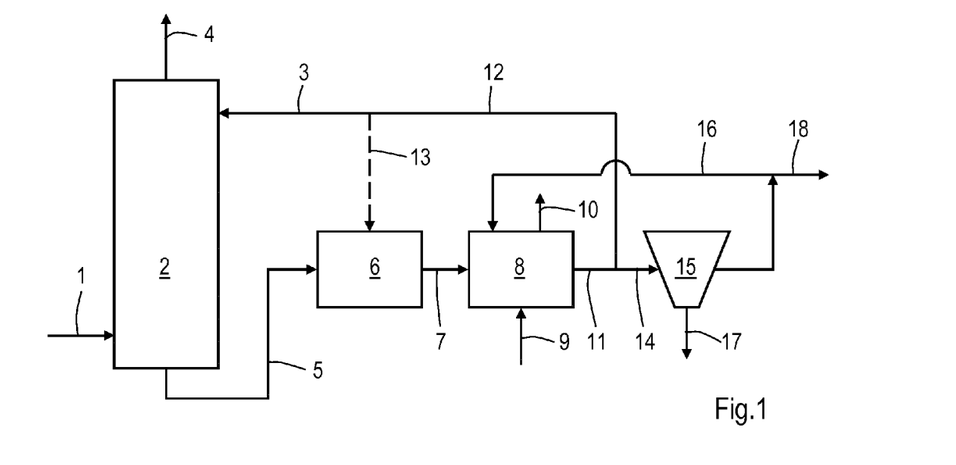
FIG. 1 shows a process line-up of an embodiment of the invention with an absorption step and first and second bioreaction zones in separate reactors.

In the process shown in FIG. 1, a sour gas stream comprising hydrogen sulphide is supplied via line 1 to absorption column 2. Liquid alkaline sorbent is supplied to the upper part of column 2 via line 3 such that the sour gas is contacted with the alkaline sorbent to obtain a treated gas stream and sorbent loaded with bisulphide. The treated gas stream is withdrawn from the column via line 4. Alkaline sorbent loaded with bisulphide is withdrawn from the bottom of column 2 via line 5 and supplied to first bioreaction zone 6. In first bioreaction zone 6, bisulphide is converted into elemental sulphur in the presence of sulphide-oxidising bacteria. During the start-up phase of the process, sulphide-oxidising bacteria may be supplied to first bioreaction zone 6 or elsewhere in the process. First liquid effluent obtained in first bioreaction zone 6 is supplied via line 7 to second bioreaction zone 8 for regeneration of the sulphide-oxidising bacteria. Air is supplied as oxidant to zone 8 via line 9. A gaseous stream comprising excess air and components stripped from the reactor liquid is withdrawn via line 10. Second liquid effluent comprising regenerated bacteria and elemental sulphur is withdrawn from second bioreaction zone 8 via line 11 and partly recycled via line 12 to the upper part of absorption column 2 to provide for regenerated liquid alkaline sorbent. With the sorbent recycle, also regenerated bacteria are recycled to absorption column 2 and indirectly to first bioreaction zone 6. Part of the liquid effluent from the second bioreaction zone may be directly recycled to first bioreaction zone 6 via line 13. Another part of the liquid effluent of zone 8 is supplied via line 14 to separator 15 wherein precipitated solid elemental sulphur is separated from the effluent to obtain sulphur-depleted second bioreaction zone effluent that is recycled via line 16 to second bioreaction zone 8. Solid elemental sulphur is withdrawn from the process via line 17. Part of the sulphur-depleted second bioreaction zone effluent is purged from the process via line 18.

The invention is also directed to a sulphur reclaiming process facility of FIG. 1 comprising:

an absorption column provided with an inlet for a sour gas, outlet for treated gas, an inlet for an alkaline liquid absorbent at its upper end and an outlet for a loaded liquid, a first anaerobic operated bioreactor having an inlet fluidly connected to the outlet for a loaded liquid and an outlet for a first liquid effluent, a second aerobic operated bioreactor provided with an inlet fluidly connected to the outlet for a first liquid effluent and an outlet for a second liquid effluent, an elemental sulphur recovery unit provided with an inlet fluidly connected to the outlet for a first liquid effluent or connected to the outlet for a second liquid effluent and outlet for elemental sulphur and an outlet for a liquid effluent poor in elemental sulphur, wherein the inlet for an alkaline liquid absorbent and are directly or indirectly connected to the outlet for a second liquid effluent.

Figure 2:
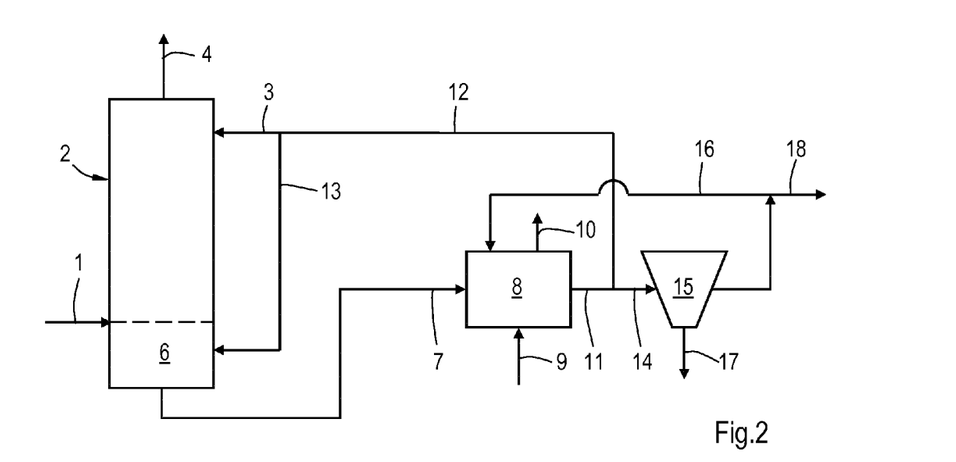
FIG. 2 shows a process line-up of an embodiment of the invention with a absorption step and with the first bioreaction zone in the lower part of the absorption column (sump of the column).

In FIG. 2 is shown a process line-up of an embodiment of the invention wherein first bioreaction zone 6 is in the lower part (sump) of absorption column 2. Corresponding reference numbers have the same meaning as in FIG. 1. In the process as shown in FIG. 2, part of the effluent of second bioreaction zone 8 is directly recycled to bioreaction zone 6 in the lower part of column 2 via line 13.

The invention is also directed to a sulphur reclaiming process facility of FIG. 2 comprising:

an absorption column provided with an inlet for a sour gas at an intermediate height along the column, an outlet for treated gas at its upper end, an inlet for an alkaline liquid absorbent at its upper end and an inlet for a second liquid at a lower elevation, wherein the inlet for the sour gas and the inlet for a second liquid substantially divides the column in an upper absorption zone and a lower anaerobic operated bioreactor having an inlet fluidly connected to the outlet of the absorption zone and to the inlet for a second liquid and an outlet for a first liquid effluent, a second aerobic operated bioreactor provided with an inlet fluidly connected to the outlet for a first liquid effluent and an outlet for a second liquid effluent, an elemental sulphur recovery unit provided with an inlet fluidly connected to the outlet for a first liquid effluent or connected to the outlet for a second liquid effluent and outlet for elemental sulphur and an outlet for a liquid effluent poor in elemental sulphur, wherein the inlet for an alkaline liquid absorbent and the inlet for a second liquid are directly or indirectly connected to the outlet for a second liquid effluent.

The invention is also directed to the above process facility comprising sulphide-oxidising bacteria, suitably in an aqueous solution.

Figures 3, 4:
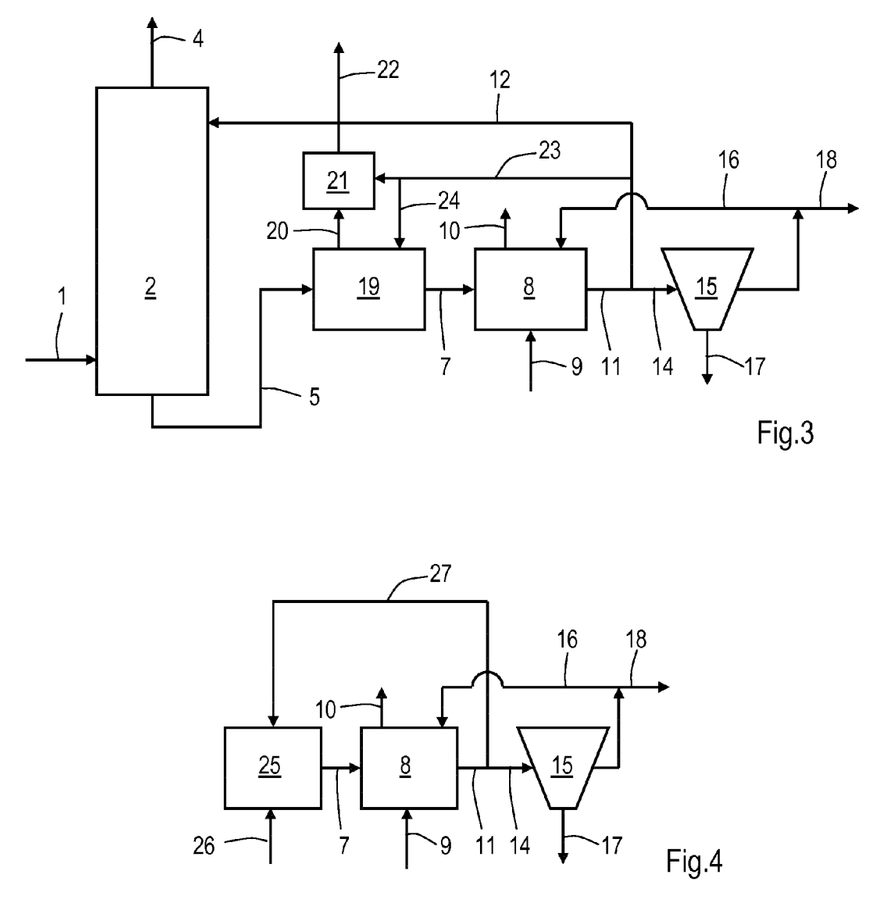
FIG. 3 shows a process line-up as in FIG. 1 wherein the first bioreaction zone is a flash vessel.
FIG. 4 shows a process line-up wherein a hydrogen sulphide comprising gas stream is directly fed to a first bioreaction zone.

In FIG. 3 a process line-up is shown of an embodiment of the invention wherein first bioreaction zone is a flash vessel 19 provided with a recontactor 21. Corresponding reference numbers have the same meaning as in FIG. 1. In such a line-up absorption column 2 is operated at an elevated pressure in order to treat a gas stream 1 having an elevated pressure. In flash vessel 19 the pressure drops and a flash gas 20 is thereby generated. The flash gas 20 may comprise hydrogen sulphide and in order to capture these compounds the gas 20 is contacted with part of the second liquid effluent 23 in recontactor 21. The thus washed gas is discharged as gas stream 22. In flash vessel 19 step (a) of the invention takes place. The resulting first liquid effluent 7 is provided to second bioreaction zone 8 to perform step (b). FIG. 3 also shows that part of the second liquid effluent 24 may be directly supplied to the flash vessel 19.

The invention will be illustrated by the following non-limiting examples.

FIG. 4 shows a process line-up wherein of an embodiment of the invention wherein to the first bioreactor 25 a stream 26 of substantially pure hydrogen sulphide comprising gas is directly fed. In bioreactor 25 step (a) is performed resulting in a first liquid effluent 7. This effluent is processed as described for FIG. 1. Part of the second effluent 11 is recycled via 27 to first bioreactor 25. Corresponding reference numbers have the same meaning as in FIG. 1.

EXAMPLE 1

In a model experiment, the conditions in the first bioreaction zone were simulated. A sample from the contents of a sulphide-oxidising bioreactor that had been operated for a year under conditions of a relatively high bisulphide load was placed in a closed glass vessel. The sulphide-oxidising bacteria in the sample were brought in an oxidised state by bubbling air through the sample for 5 minutes. Then, the air supply was stopped and nitrogen was bubbled through the sample to remove any dissolved oxygen and to create an anaerobic condition. Subsequently, a bisulphide solution was added to the sample with oxidised (regenerated) bacteria such that a concentration of a gram 1 gram bisulphide per liter was obtained. Within 30 seconds after addition of the bisulphide solution, flocks of elemental sulphur appeared.

EXAMPLE 2

Fed-batch experiments were performed in a 5 L experimental setup. In the first experiment, two bioreactors were operated in the way as described by step (a) and (b), i.e. the first anaerobic bioreactor with supply of $H_2S$ and the second bioreactor with supply of oxygen; solution was recycled from the second bioreactor to the first bioreactor. In this line up 97.8 mol % of all added $H_2S$ was converted to elemental sulphur and only 2.2% was converted to other sulphur compounds, such as sulphate and thiosulfate.

COMPARATIVE EXPERIMENT

Experiment 2 was repeated in one bioreactor with simultaneous supply of $H_2S$ and oxygen. Thus only one aerobic operated bioreactor was used. In this experiment the maximum yield for elemental sulphur was 88.0 mol % of all added $H_2S$. Additionally, significant amounts of sulphate (5.8 mol %) and thiosulphate (6.2 mol %) were formed. These experiments showed that the selectivity for elemental sulphur is strongly increased when the process is operated with step (a) and (b) as described in this invention.

The invention claimed is:

1. A process for the biological conversion of bisulphide into elemental sulphur, comprising the following steps:
    a) converting bisulphide as dissolved in an aqueous solution to elemental sulphur in the presence of sulphide-oxidising bacteria and under anaerobic conditions wherein the concentration of molecular oxygen in the aqueous solution is at most 1 µM to obtain a first liquid effluent comprising elemental sulphur and used sulphide-oxidising bacteria;
    b) regenerating the used sulphide-oxidising bacteria as obtained in step (a) and as comprised in an aqueous solution in the presence of an oxidant to obtain a second liquid effluent comprising regenerated sulphide-oxidising bacteria;
    c) separating elemental sulphur from either the first and/or the second liquid effluent;
    d) using the regenerated sulphide-oxidising bacteria in step (a) as the sulphide-oxidising bacteria.

2. The process according to claim 1, wherein the concentration of molecular oxygen in the aqueous solution is at most 0.1 µM in step (a).

3. The process according to claim 1, wherein more than 80 mol % of the dissolved bisulphide is removed from the aqueous solution by biological remediation by the sulphide-oxidising bacteria in step (a).

4. The process according to claim 1, wherein the bisulphide concentration in the aqueous solution as supplied to step (a) is in the range of from 100 mg/L to 15 g/L.

5. The process according to claim 1, wherein the first liquid effluent comprises less than 5 mM dissolved bisulphide.

6. The process according to claim 1, wherein the bisulphide comprising aqueous solution of step (a) is obtained by directly supplying a hydrogen sulphide comprising gas to a vessel in which step (a) is performed.

7. The process according to claim 1, wherein the bisulphide comprising aqueous solution of step (a) is obtained by contacting an alkaline absorbent with a sour gas comprising sulphur compounds including hydrogen sulphide.

8. The process according to claim 7, wherein the alkaline absorbent comprises the regenerated sulphide-oxidising bacteria of the second liquid effluent.

9. The process according to claim 8, wherein the process comprises an absorption step for absorption of sulphide from a sour gas stream, at least part of the second liquid effluent is indirectly recycled to step (a) by first recycling at least part of the second liquid effluent to an upper part of the absorption column as used in the absorption step.

10. The process according to claim 7, wherein the liquid alkaline absorbent is a buffered solution comprising sodium carbonate and sodium bicarbonate or potassium carbonate and potassium bicarbonate or their mixtures.

11. The process according to claim 1, wherein the oxidant in step (b) is molecular oxygen.

12. The process according to claim 1, wherein the process is a continuous process.

13. The process according to claim 1, wherein in step (c) elemental sulphur is recovered from at least part of the second liquid effluent to obtain elemental sulphur and sulphur-depleted second effluent and wherein at least part of the sulphur-depleted second effluent is recycled to the process in step (d).

14. The process according to claim 13, wherein at least part of the sulphur-depleted second effluent is recycled directly to step (b).

15. The process according to claim 1, wherein at least part of the second liquid effluent and/or of the sulphur-depleted second effluent is purged from the process.

16. The process according to claim 15, wherein the at least part of the second liquid effluent and/or of the sulphur-depleted second effluent that is purged from the process is first subjected to a membrane separation step to obtain a retentate stream comprising sulphide-oxidising bacteria and a permeate stream that is essentially free of sulphide-oxidising bacteria and wherein the retentate stream is recycled to the process and the permeate stream is purged from the process.

17. The process according to claim 16, wherein at least part of the sulphur-depleted second effluent is purged from the process and is subjected to the membrane separation step.

18. The process according to claim 1, wherein step (a) and step (b) are performed in a separate bioreactor.

19. A sulphur reclaiming process facility comprising
an absorption column provided with an inlet for a sour gas, outlet for treated gas, an inlet for an alkaline liquid absorbent at its upper end and an outlet for a loaded liquid,
a first anaerobic operated bioreactor having an inlet fluidly connected to the outlet for a loaded liquid and an outlet for a first liquid effluent,
a second aerobic operated bioreactor provided with an inlet fluidly connected to the outlet for a first liquid effluent and an outlet for a second liquid effluent,
an elemental sulphur recovery unit provided with an inlet fluidly connected to the outlet for a first liquid effluent or connected to the outlet for a second liquid effluent and outlet for elemental sulphur and an outlet for a liquid effluent poor in elemental sulphur, wherein the inlet for the alkaline liquid absorbent are directly or indirectly connected to the outlet for a second liquid effluent and wherein the first anaerobic operated reactor is directly connected to the outlet for a second liquid effluent.

20. The process facility according to claim 19 comprising sulphide-oxidising bacteria.

21. A sulphur reclaiming process facility comprising:
an absorption column provided with an inlet for a sour gas at an intermediate height along the column, an outlet for treated gas at its upper end, an inlet for an alkaline liquid absorbent at its upper end and an inlet for a second liquid at a lower elevation, wherein the inlet for the sour gas and the inlet for a second liquid substantially divides the column in an upper absorption zone and a lower anaerobic operated bioreactor having an inlet fluidly connected to the outlet of the absorption zone and to the inlet for a second liquid and an outlet for a first liquid effluent,
a second aerobic operated bioreactor provided with an inlet fluidly connected to the outlet for a first liquid effluent and an outlet for a second liquid effluent,
an elemental sulphur recovery unit provided with an inlet fluidly connected to the outlet for a first liquid effluent or connected to the outlet for a second liquid effluent and outlet for elemental sulphur and an outlet for a liquid effluent poor in elemental sulphur, wherein the inlet for an alkaline liquid absorbent and the inlet for a second liquid are directly or indirectly connected to the outlet for a second liquid effluent.

22. The process facility according to claim 21 comprising sulphide-oxidising bacteria.

* * * * *